(12) United States Patent
Holmgren et al.

(10) Patent No.: US 8,679,558 B2
(45) Date of Patent: Mar. 25, 2014

(54) PROBIOTIC JUICE DRINK

(75) Inventors: Kerstin Holmgren, Helsingborg (SE); Marie Lindgren, Kopingebro (SE)

(73) Assignee: Probi AB, Lund (SE)

( * ) Notice: Subject to any disclaimer, the term of this patent is extended or adjusted under 35 U.S.C. 154(b) by 0 days.

(21) Appl. No.: 13/320,452

(22) PCT Filed: May 12, 2010

(86) PCT No.: PCT/SE2010/050525
§ 371 (c)(1),
(2), (4) Date: Mar. 2, 2012

(87) PCT Pub. No.: WO2010/132017
PCT Pub. Date: Nov. 18, 2010

(65) Prior Publication Data
US 2012/0171329 A1 Jul. 5, 2012

Related U.S. Application Data

(60) Provisional application No. 61/179,457, filed on May 19, 2009.

(30) Foreign Application Priority Data

May 14, 2009 (SE) ...................... 0950341

(51) Int. Cl.
*A23L 2/02* (2006.01)
(52) U.S. Cl.
USPC ........................................... 426/61
(58) Field of Classification Search
USPC ........................................... 426/61
See application file for complete search history.

(56) References Cited

U.S. PATENT DOCUMENTS

| | | | |
|---|---|---|---|
| 2002/0122847 A1* | 9/2002 | Nunes et al. | 426/72 |
| 2007/0098847 A1 | 5/2007 | Teissier | |
| 2007/0128328 A1 | 6/2007 | Tanada et al. | |
| 2008/0206403 A1 | 8/2008 | Beverini et al. | |
| 2009/0208469 A1* | 8/2009 | Alenfall et al. | 424/93.45 |
| 2010/0086646 A1 | 4/2010 | Francois et al. | |

FOREIGN PATENT DOCUMENTS

| | | |
|---|---|---|
| CN | 101088421 | 12/2007 |
| EP | 0166238 A1 | 1/1986 |
| JP | H 06-501624 | 2/1994 |
| JP | 2007-195414 | 8/2007 |
| JP | 2007-195415 | 8/2007 |
| JP | 2007-527724 | 10/2007 |
| JP | 2008-541774 | 11/2008 |
| JP | 2009-511470 | 3/2009 |
| WO | WO 93/08123 | 2/1993 |
| WO | WO 2005/092127 | 10/2005 |
| WO | WO 2006/131569 | 12/2006 |
| WO | WO 2007-040445 | 4/2007 |
| WO | WO-2008068341 A1 | 6/2008 |
| WO | WO 2008/134626 | 11/2008 |

OTHER PUBLICATIONS

JP-2007-195414-Machine Translation.*
International Preliminary Report on Patentability and Written Opinion dated Nov. 24, 2011 issued in corresponding International Application No. PCT/SE2010/050525.
Vivien M. Sheehan et al., "Assessing the acid tolerance and the technological robustness sof probiotic cultures for fortification in fruit juices," *ScienceDiet, Innovative Food Science & Emerging Technologies*, vol. 8, pp. 279-284 (2007).
Sortimentlista (online) Aria Foods, p. 9, art. No. 6965 (May 4, 2009).
ProViva (online) Skanemejerier AB, p. 3, art. No. 891 (2009).
Examination Report dated May 11, 2012 issued in corresponding New Zealand Application No. 596584.
http://www.naturallynovascotia.com/products/viewproduct.asp?productid=136, published Oct. 22, 2008.
English translation of Notice of Rejection dated May 8, 2012 issued in corresponding Japanese Application No. 2012-510778.

* cited by examiner

*Primary Examiner* — D. Lawrence Tarazano
*Assistant Examiner* — Hamid R Badr
(74) *Attorney, Agent, or Firm* — Harness, Dickey & Pierce, P.L.C.

(57) ABSTRACT

A probiotic fruit juice drink consisting of at least one species of probiotic bacteria chosen from *Lactobacillus* and at least one gas formation reducer chosen from acerola, pomegranate, cranberry, arqnia, blackcurrant, buckthorn or elderberry and any combination thereof and a primary fruit juice chosen from a citrus fruit juice or an pip fruit juice. The probiotic juice drink contains optionally a secondary fruit juice and optionally water.

18 Claims, 5 Drawing Sheets

Malolactic fermentation

Fig. 5

PROBIOTIC JUICE DRINK

CROSS-REFERENCE TO RELATED APPLICATIONS

This application is a national phase under 35 U.S.C. §371 of PCT International Application No. PCT/SE2010/050525 which has an International Filing Date of May 12, 2010, which claims priority under 35 U.S.C. §119 to U.S. Provisional Application No. 61/179,457, filed May 19, 2009.

TECHNICAL FIELD OF THE INVENTION

The present invention relates to a probiotic fruit juice drink, especially a probiotic orange or apple juice, which has a good taste and has a long shelf-life. The probiotic fruit juice drink further has beneficial effects on the health of the consumer.

BACKGROUND ART

Probiotic bacteria are defined as live microorganisms which when administered in adequate amounts beneficially affect the host. *Lactobacilli* and *bifidobacteria* are the most frequently used bacteria in probiotic products. These bacteria are generally safe, as are probiotics based on these organisms. Intake of different probiotic bacteria has been shown to have clinical benefits in various physiologic or pathologic situations. For a bacterium to fulfill the probiotic definition it has to be able to survive in and colonize the intestines, survive the harsh processes at production and storage of the food, but there also has to be clear evidence that it has positive effects on the health of the consumer.

Figure 1:
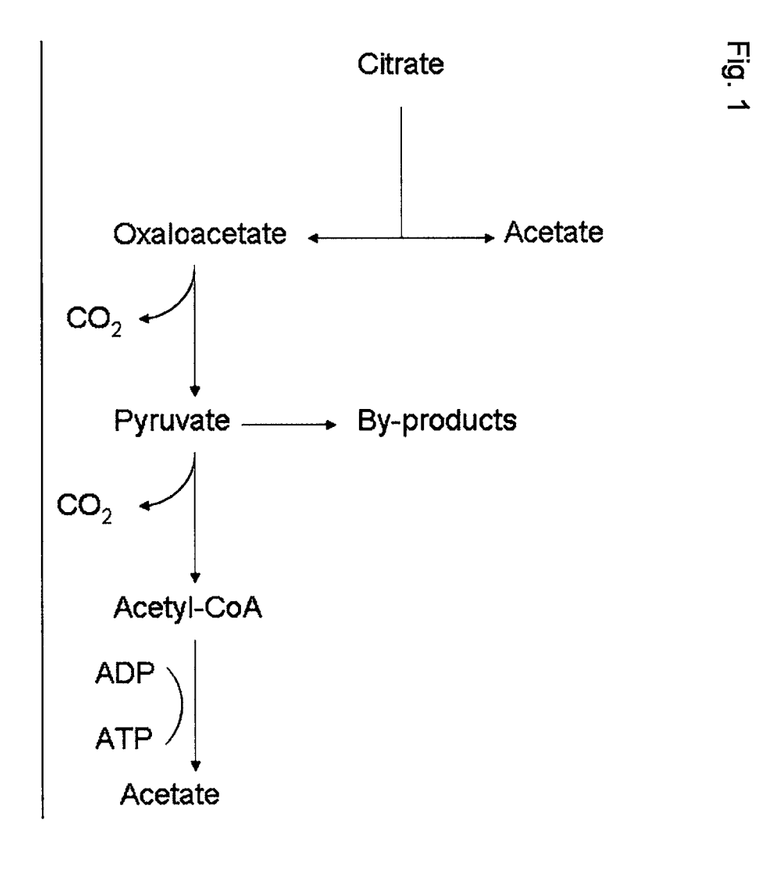
FIG. 1 depicts the metabolization of citrate (the salt of citric acid) to carbon dioxide and acetate.
Figure 2:
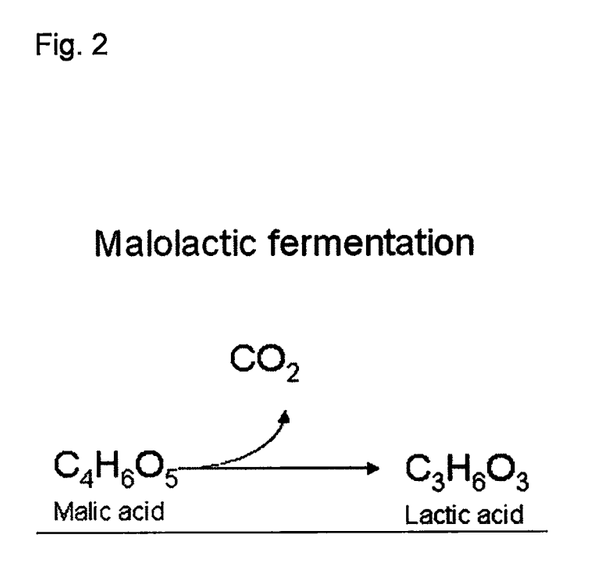
FIG. 2 depicts the metabolization of malic acid to carbon dioxide and lactic acid.

It is known in the prior art that bacteria of the genus *Lactobacillus* metabolize organic acids present in fruits and fruit juices. The metabolization causes the formation of gas such as carbon dioxide. The organic acid, citric acid, is present in high concentrations in citrus fruits and citrus fruit juices such as orange and lemon juice. The organic acid, malic acid, is present in high concentrations in apples and apple juice. A product of orange juice or apple juice or the like with a species of *Lactobacillus* has not been possible to manufacture before in view of the large amount of gas produced (carbon dioxide), causing a very short shelf-life as well as a change of taste. The gas development causes bombage of the package, which means that the package is expanded due to the higher pressure inside the package caused by the carbon dioxide produced therein. Furthermore, the taste of the product is deteriorated because of the sparkling and fizzy form the product takes in view of the metabolization of the organic acids. The metabolization of malic acid and citric acid results in lactic acid and acetic acid, in addition to carbon dioxide, see FIG. 1-3, causing unpleasant off-tastes in the product. Both apple and orange juice are very popular juices to drink in the west world, especially in the morning. In view of the above problems, a probiotic apple or orange juice has not been possible to manufacture and distribute before.

ProViva® is a commercially available probiotic fruit- and oat based product comprising *Lactobacillus Plantarum* 299v. These products cannot contain too high amounts of fruits containing the organic acids, citric acid and malic acid, due to the above mentioned problem, i.e. gas production. Thus, these products do not include fruit juices such as apple, orange or exotic multi-fruit juices. Furthermore, Proviva® is not a pure juice.

Naked Juice Company has a probiotic tropical mango juice (100%) on the market comprising a species of *Bifidobacterium* as well as juice from apple, mango, orange, banana and pineapple. *Bifidobacterium* are very sensitive to low pH environments and most of the bacteria cannot handle an acidic environment below 4 and die. The metabolism of *Bifidobacterium* differs from that of *Lactobacillus*.

In US2008/0206403 a method as well as probiotic food products are described, which products have been depleted of organic acids in order to reduce the production of carbon dioxide from the final food product. Depleting organic acids from a fruit is performed by selecting a fruit-based matrix having a low natural acidity.

In US 2007/0128328 the use of a bacterial growth inhibitor or bacterostatic agent comprising acerola against thermo-resistant and acid-resistant (TAB) bacteria belonging to the genus *Alicyclobacillus* is disclosed. Bacteria of the genus *Alicyclobacillus* are known to be resistant to general pasteurization and can therefore cause undesirable odours and a decrease in food quality in a final pasteurized product. *Alicyclobacillus acidoterrestris* and *Alicyclobacillus acidocaldarius* are thermo-acidophilic, non-pathogenic, spore-forming bacteria that can survive the typical heat processing of fruit juices and concentrates. Bacterial endospores then germinate, grow and cause spoilage of acid food products.

Thus, there remains a need within the technical field to provide probiotic fruit juice drinks that can handle survival of the probiotic bacteria in the acidic environment of the fruit juice drink, the probiotic bacteria still provide beneficial effects in the gastrointestinal tract and the fruit juice drink still has a good taste and long shelf-life, i.e. non-bombage of the package. There is no such product available on the market today.

Thus, the object of the present invention is to provide a probiotic fruit juice drink with good taste and long shelf-life. The juice drink is further stable and the previous problems with gas production have been solved.

SUMMARY OF THE INVENTION

Thus, one object of the present invention is to provide a probiotic fruit juice drink consisting of at least one species of probiotic bacteria chosen from *Lactobacillus* and at least one gas formation reducer chosen from acerola, pomegranate, cranberry, aronia, blackcurrant, buckthorn, sloe or elderberry or any combination thereof and a primary fruit juice and optionally a secondary fruit juice and optionally water. Thus, a probiotic fruit juice drink with good taste has surprisingly been possible to manufacture in accordance with the present invention. The previous problems with citric acid and malic acid in the presence of a strain of *Lactobacillus* have been solved.

A further object of the present invention is the use of at least one gas formation reducer chosen from acerola, pomegranate, cranberry, aronia, blackcurrent, buckthorn, sloe, or elderberry or any combination thereof for producing a probiotic fruit juice drink consisiting of, in addition to the gas formation reducer, at least one species of probiotic bacteria chosen from *Lactobacillus* and a primary fruit juice and optionally a secondary fruit juice and optionally water.

DETAILED DESCRIPTION OF THE INVENTION

According to the present invention a probiotic fruit juice drink consisting of at least one species of probiotic bacteria chosen from *Lactobacillus* and at least one gas formation reducer chosen from acerola, pomegranate, cranberry, aronia, blackcurrant, buckthorn, sloe or elderberry or any combination thereof and a primary fruit juice and optionally a secondary fruit juice and optionally water has been provided. In accordance with experiments that have been performed below the gas formation reducers have been shown to reduce the formation of carbon dioxide in juice drinks in the presence of both a strain of *Lactobacillus* as well as a fruit juice containing high amounts of the organic acids, citric acid or malic acid, e.g. orange juice or apple juice. As have been described above and in FIG. 1-3 the strain of *Lactobacillus* metabolizes these organic acids to carbon dioxide and acetic acid and lactic acid, respectively, to a high extent in normal cases. However, in accordance with the present invention the production of carbon dioxide has been reduced in the presence of the particular gas formation reducers, as mentioned herein.

Thus, by the observations that have been made it has now surprisingly been found that it is possible to provide a probiotic fruit juice drink, especially a probiotic orange or apple juice. A long-felt need within the technical field of probiotics has been fulfilled by the present invention since it has not been possible before to manufacture a product of the present invention before.

In the present context the phrase "gas formation reducer" is meant to describe that the amount of gas, preferably carbon dioxide, is reduced in the juice product compared to a product without the addition of the gas formation reducer. Further indications of the fact that the amount of carbon dioxide has been reduced are that the product is no longer sparkling and fizzy, such as a carbonated drink, and bombage of the package does not take place during the shelf-life of the product. By adding the gas formation reducer to a primary fruit juice in the presence of probiotics according to the invention the juice is transformed to a state where carbon dioxide is not produced to such a high extent as before. The formation of diacethyl as an off-flavour can also be reduced in the present context, especially when the probiotic *Lactobacillus paracasei* is used in the juice drink. When *Lactobacillus paracasei* metabolises citrate, diacethyl is formed. Diacethyl in a juice drink has an unpleasant taste. It has been observed in the experiments performed that the off-flavour caused by diacethyl has been reduced in a juice drink of the present invention.

Therefore, a probiotic fruit juice with long shelf-life and good taste can be manufactured.

The gas formation reducers are chosen from acerola, pomegranate, cranberry, aronia, blackcurrant, buckthorn, sloe or elderberry or any combination thereof. These reducers may be added in the form of a fruit concentrate or a fruit pure or as juice. If a fruit concentrate of the gas reducer, e.g. acerola, is used water is usually added to the concentrate so that the concentrate is diluted to a concentration being equal to or resembles the original fruit juice. The scientific name of pomegranate is *Punica granatum* L. The scientific name of Acerola is *Malpighia emarginata* DC, but *Malpighiaceae punicifolia* L. and *M. glabla* L. is also referred to sometimes. The scientific name of cranberry is *Vaccinium macrocarpo*.

In an embodiment of the invention the primary fruit juice is a citrus fruit juice, wherein the citrus fruit juice is chosen from orange juice, lemon juice, grapefruit juice, and lime juice, or a pip fruit juice, wherein the pip fruit juice is chosen from apple juice and pear juice.

In another embodiment of the invention the at least one species of probiotic bacteria is chosen from the group comprising *Lactobacillus plantarum, Lactobacillus rhamnsosus*, and *Lactobacillus paracasei*. The species of *Lactobacillus* may also be chosen from *Lactobacillus acidophilus, Lactobacillus casei, Lactobacillus bulgaricus, Lactobacillus helveticus* and *Lactobacillus reuteri*.

The at least one species of *Lactobacillus plantarum* is preferably chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

The *Lactobacillus plantarum* strains mentioned above have all been deposited at Deutsche Sammlung von Mikroorganismen von Zellkulturen GmBH. *Lactobacillus plantarum* 299, deposition number DSM 6595, was deposited on 16 Mar. 1995. *Lactobacillus plantarum* HEAL 9, DSM 15312, *Lactobacillus plantarum* HEAL 19, DSM 15313, and *Lactobacillus plantarum* HEAL 99, DSM 15316 were deposited on 28 Nov. 2002.

The at least one species of *Lactobacillus paracasei* is preferably chosen from the group comprising *Lactobacillus paracasei* 8700:2, DSM 13434, and *Lactobacillus paracasei* 02A, DSM13432. *Lactobacillus paracasei* 8700:2, DSM 13434, and *Lactobacillus paracasei* 02A, DSM13432 were deposited on 6 Apr. 2000 at Deutsche Sammlung von Mikroorganismen von Zellkulturen GmBH.

The at least one species of *Lactobacillus* rhamnosus is preferably chosen from *Lactobacillus rhamnosus* 271, DSM 6594. *Lactobacillus rhamnosus* 271, DSM 6594, and *Lactobacillus plantarum* 299v, deposition number DSM 9843 were deposited at Deutsche Sammlung von Mikroorganismen von Zellkulturen GmBH on 25 Mar. 1996.

In an embodiment of the invention the at least one species of probiotic *Lactobacillus* is present in the fruit juice drink in an amount of about $1 \times 10^5$ to about $1 \times 10^{12}$ CFU per serving (250 ml), preferably from about $1 \times 10^6$ to about $1 \times 10^{10}$ CFU per serving, and more preferably from about $1 \times 10^7$ to about $1 \times 10^9$ CFU per serving. CFU stands for colony forming units of viable bacterial numbers per serving.

In another embodiment of the invention the secondary fruit juice is chosen from juice of pineapple, mango, banana, white grape, peach, apricot, passion fruit, watermelon, raspberry, strawberry, blueberry, blackberry, kiwi, or guava or any mixture thereof. The secondary fruit juice has the function of effecting taste of the fruit drink in a case where for instance the taste of the gas formation reducer is too distinct.

In a yet further embodiment the fruit juice drink additionally contains water to provide a more diluted and cost effective product.

The proportion of the primary fruit juice may present in the range of about 50-100% (w/w), preferably about 75-100% (w/w), and more preferably about 90-100% (w/w), the gas formation reducer may present in the range of about 0.5-40% (w/w), preferably about 0.5-30% (w/w), and more preferably about 0.5-20% (w/w), water may present in the range of about 0-49% (w/w), preferably about 0-30% (w/w), and more preferably 0-20% (w/w), and the secondary fruit juice is present in the range of 0-10% (w/w), preferably 0-5% (w/w).

In another embodiment of the invention vitamin C is additionally added to the juice drink. This is done in instances where for instance a proportion of the vitamin C in the natural juices present is lost during production.

In an embodiment of the invention a probiotic fruit juice drink is provided, wherein the fruit juice is apple juice and the gas formation reducer is pomegranate juice and the strain of Lactobacillus is Lactobacillus plantarum, Lactobacillus rhamnsosus, or Lactobacillus paracasei. Thus, a 100% fruit juice of apple and pomegranate is provided with the addition of probiotic bacteria.

In another embodiment of the invention a probiotic fruit juice drink is provided, wherein the fruit juice is orange juice and the gas formation reducer is acerola juice and the strain of Lactobacillus is Lactobacillus plantarum, Lactobacillus rhamnsosus, r Lactobacillus paracasei. Thus, a 100% fruit juice of orange and acerola is provided with the addition of probiotic bacteria.

In an embodiment of the invention the fruit juice drink may be a 100% fruit juice containing, in addition to the 100% fruit juice, only probiotics. A 100% fruit juice is a liquid naturally contained in fruit or fruit tissue. Juice is prepared by mechanically squeezing or macerating fresh fruits without the application of heat or solvents. For example, orange juice is the liquid extract of the fruit of the orange tree. Juice may be prepared in the home from fresh fruits and vegetables using variety of hand or electric juicers. Many commercial juices are filtered to remove fiber or pulp, but high pulp fresh orange juice is a popular beverage. Juice may be marketed in concentrate form, sometimes frozen, requiring the user to add water to reconstitute the liquid back to its "original state". In the manufacture of a fruit juice of the present invention a fresh juice type as well as concentrate juice type may be used so that the final juice product in both cases fall within the definition of a 100% fruit juice containing additionally only probiotics. In the present context this would mean for instance that a 100% fruit juice of orange and acerola is provided with a probiotic species of Lactobacillus, as described herein, in an amount, as described herein. Alternatively, a 100% fruit juice of apple and pomegranate is provided with a probiotic species of Lactobacillus, as described herein, in an amount, as described herein.

Most nations define a standard purity for a beverage to be considered a "fruit juice." This name is commonly reserved for beverages that are 100% pure fruit juice. In the present context the 100% fruit juice is a 100% pure fruit juice with the addition of probiotics in the amounts as described herein.

In the case of using a concentrate in the manufacturing process of the fruit juice drink of the present invention it may in certain instances be beneficial to add add-back flavors and/or aromas to the product. It is known that in the manufacturing process of a fruit concentrate volatile flavor compounds are lost and the juice can taste flat and cooked. Adding such add-back flavors or aromas to the final product restores the fresh taste of the juice. Such additions are within the scope of the present invention since the function of these additions is to restore the original taste of the 100% fruit juice or fruit juice drink. Examples of such add-back flavors are manufactured by Mastertaste Inc., US and examples that can be mentioned here are OR4687 (Orange Juice Flavor Special 4687), OR4692 (Orange Add-back Special 4692), OR4914 (Orange Oil Blend 4914), OR5001 (Orange Aroma), OR5010 (Orange Aroma Premium 10).

DETAILED DESCRIPTION OF EMBODIMENTS OF THE INVENTION

Experimental

Production of Probiotic Fruit Juice

The different components of the fruit juice drinks (gas formation reducer, primary juice and optionally secondary juice) were mixed to the concentrations given below and pasteurized (85° C., 15 seconds) and thereafter cooled to 8° C. However, in a full-scale production the pasteurization would be made at 92° C., 10 seconds.

After cooling the fruit juice mixture the freeze dried bacteria (Probi AB) were added to give a concentration between $0.1 \times 10^9$-$10 \times 10^9$ cfu (colony forming units)/250 ml juice. The resulting probiotic fruit juice was well mixed before it was packaged.

The fruit juices were stored at 4° C. or 8° C. for stability test and sensory evaluation for 10 weeks and 6 weeks, respectively.

To determine the fruit juices ability to form carbon-dioxide and off-taste during storage an accelerated shelf life test (Skanemejerier, Sweden) was used (5 days, 25° C.). This is a predictive test for evaluating if certain juice-mixtures may develop off-taste and gas-formation. If the concentration of $CO_2$ is below 25% it is considered that the product will not cause any gas formation when stored 4° C. or 8° C. for 10 weeks and 6 weeks respectively.

350 ml plastic bottles were filled with 250 ml each of the probiotic fruit juice. The bottles were then incubated for 5 days at 25° C. After the 5 days of incubation the $CO_2$ concentration was measured (Check point II, PBI Dansensor) in the head-space. After ceased $CO_2$ measurements the bottles were opened and a sensory evaluation was made on the juices. Additional shelf life trials on fruit juices where the carbon dioxide was below 25% were conducted at 4° C. or 8° C. for 10 weeks and 6 weeks respectively. The cell count was measured according to the standard method used at Skanemejerier, Sweden. This includes analyzing the samples by plate count method (3 days, 37° C.) on MRS agar on day 14 (Skanemejerier, Sweden).

The Reducing Effect of Different Gas Formation Reducers Added in Orange Juice on the Probiotic Bacteria.

Figure 3:
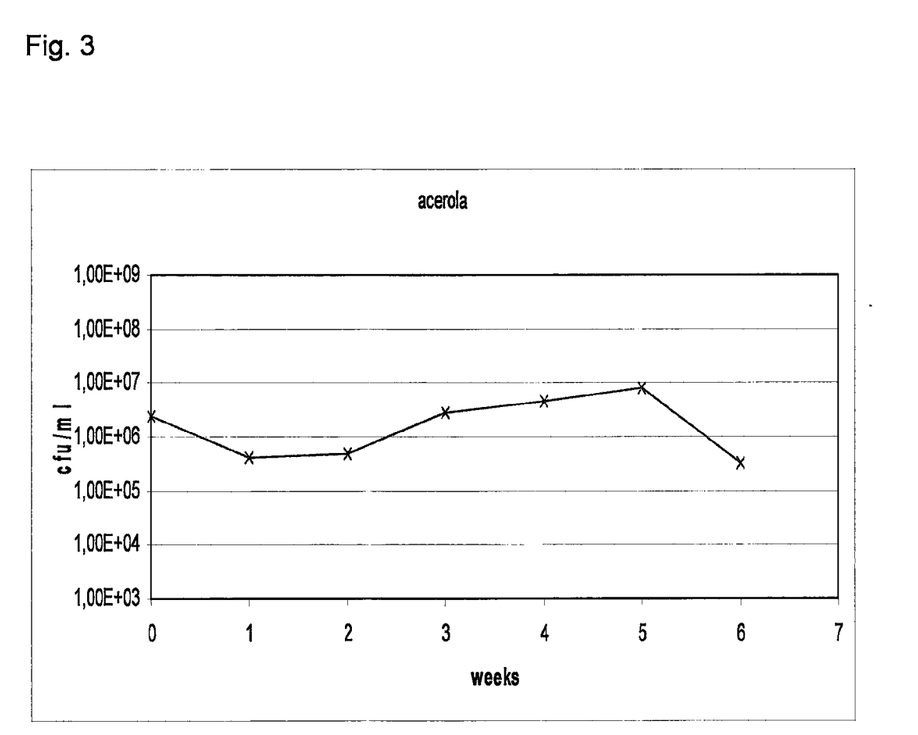
FIG. 3 depicts the shelf life of a probiotic mixture of *Lactobacillus plantarum* HEALS and *Lactobacillus para-* casei 8700:2 ($10^9$ cfu) in an orange juice with 10% (weight) added acerola during storage at 8° C.

Different gas formation reducers (cranberry, cow berry, acerola)) were added to a primary juice (orange juice) and probiotic bacteria were added after heat-treatment (see experimental set-up above). The carbon dioxide formation and sensory evaluation were measured in an accelerated shelf life test after 5 days of incubation at 25° C. (table 1). Only acerola had the potential to inhibit formation of gas and off-flavour. The storage stability was followed in the orange acerola juice during 6 weeks at 8° C. (FIG. 3). The bacteria remained stable throughout the whole shelf live and no off-flavour was noticed. Table 1 shows the evaluation of sensory properties and formation of carbon dioxide ($CO_2$) in juices with or without different added "gas formation reducers". The juices were inoculated with a total amount of 5e6 cfu/ml of L. plantarum HEAL 9 and L. paracasei 8700:2.

TABLE 1

| Juice components (weight %) | sensory evaluation | $CO_2$ (%) |
| --- | --- | --- |
| 100% orange juice | + | 45 |
| 20% cranberry + 80% orange juice | + | 40 |
| 20% cowberry + 80% orange juice | + | 38 |
| 10% Acerola + 90% orange juice | OK | 20 |

+ denotes unpleasant stickiness of the product
OK denotes a pleasant feeling.

Additional experiments were made with different additions of acerola, 5%, 10%, 15%, and 20% (by weight) to the orange juice. Totally $1\times10^9$ cfu of *L. plantarum* HEAL 9 and *L. paracasei* 8700:2 was added to the juice and the carbon dioxide were measured after 5 days at 25° C. Results are shown in Table 2.

TABLE 2

| Juice | pH | $CO_2$ | Sensory evaluation |
|---|---|---|---|
| 95% Orange juice/Acerola 5% | 3.9 | <25% | OK |
| 90% Orange/10% Acerola | 3.8 | <25% | OK |
| 85% Orange/15% Acerola | 3.8 | <25% | OK |
| 80% Orange/20% Acerola | 3.8 | <25% | OK |

+ denotes unpleasant stickiness of the product.
Ok denotes pleasant feeling.

Experiment with Addition of Different Amounts of Cranberry Juice or Pomegranate to Apple Juice.

Figure 4:
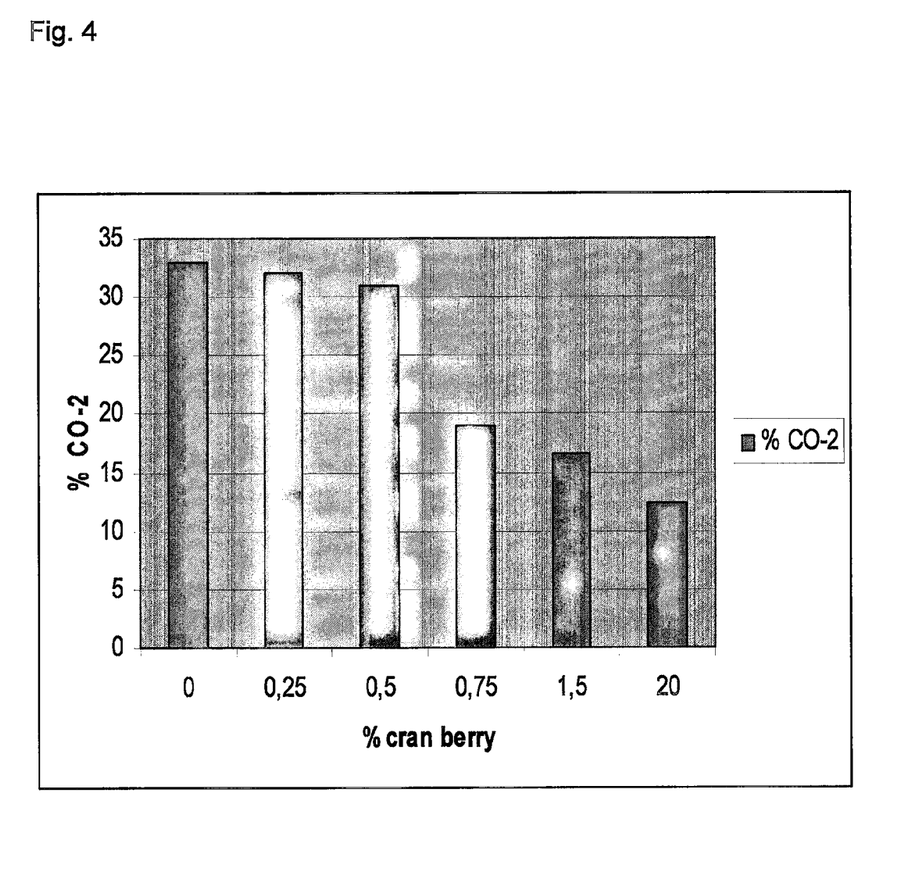
FIG. 4 depicts the carbon dioxide produced in apple juice in the presence of cranberry at different concentrations.
Figure 5:
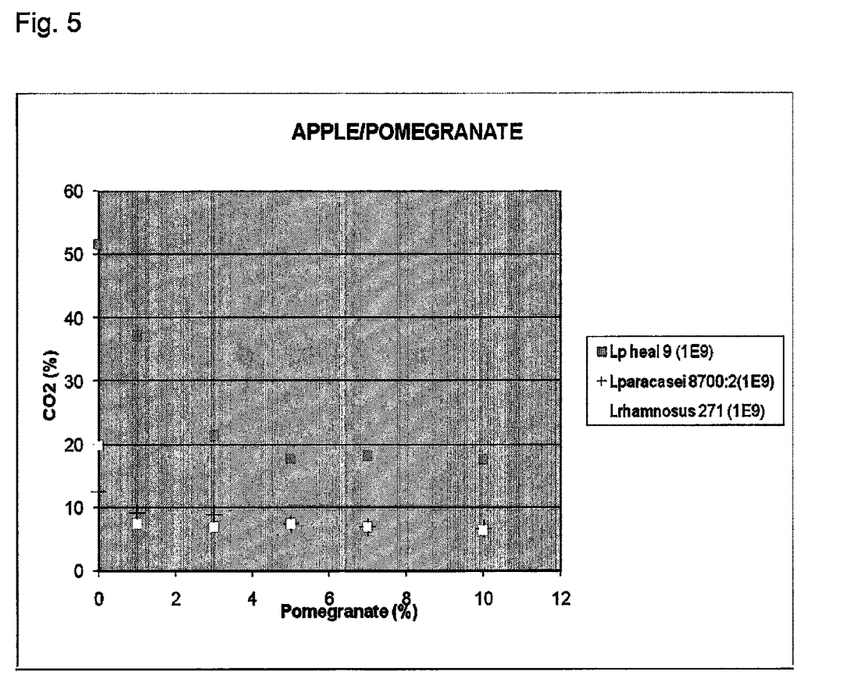
FIG. 5 depicts the carbon dioxide produced in apple juice in the presence of pomegranate at different concentrations.

Different amounts of gas formation reducers (cranberry) were added to samples of primary juice (apple juice). A sensory evaluation and measurement of carbon dioxide formation in the juice were performed in an accelerated shelf life test after 5 days of incubation at 25° C., see Table 3. The metabolism of the probiotic bacteria was slowed down without a reduction of their viability in a narrow range of 0.75-1.5% addition of the gas formation reducer (cranberry) (Table 3 and FIG. 4). Beyond this narrow range the bacteria were either inhibited by the cranberry or grew excessively causing formation of off-flavour. The effect of another added gas formation reducer (pomegranate juice) was also studied. The addition of pomegranate juice slowed down the metabolism as well as carbon dioxide formation which was below 25%. Table 3 shows the carbon dioxide formation and sensory evaluation and survival after 3 weeks at 8° C. in a probiotic apple juice with different amount of cranberries. The juices were inoculated with 5e6 cfu/ml of *L. plantarum* HEAL 9 and *L. paracasei* 8700:2.

| Cranberry (wt %) | $CO_2$ (%) | Sensory evaluation | CFU after 3 weeks |
|---|---|---|---|
| 0 | 33 | + | |
| 0.25 | 32 | + | 5.8E+06 |
| 0.5 | 31 | + | 3.9E+06 |
| 0.75 | 19 | OK | 3.5E+04 |
| 1.5 | 16.5 | OK | 1.9E+02 |
| 20 | 12.4 | bitter | |

+ denotes unpleasant stickiness of the product.
Ok denotes pleasant feeling.

Table 3 a)-c) show the carbon dioxide formation in a probiotic apple juice with different amounts of pomegranate. The probiotics used in the three apple juice/pomegranate experiments are *Lactobacillus plantarum* HEAL 9, *Lactobacillus paracasei* 8700:2 or *Lactobacillus rhamnosus* 271.

TABLE 3a

*Lactobacillus plantarum* HEAL 9, $1 \times 10^9$ CFU/serving.

| Fruit juice components (wt %) | $CO_2$ (%) | Lp HEAL 9 (CFU/250 ml) |
|---|---|---|
| 100% apple/ | 52 | $6.5 \times 10^9$ |
| 99% apple/1% pomegranate | 37 | $6.0 \times 10^9$ |

TABLE 3a-continued

*Lactobacillus plantarum* HEAL 9, $1 \times 10^9$ CFU/serving.

| Fruit juice components (wt %) | $CO_2$ (%) | Lp HEAL 9 (CFU/250 ml) |
|---|---|---|
| 97% apple/3% pomegranate | 21 | $2.5 \times 10^8$ |
| 95% apple/5% pomegranate | 18 | $1.7 \times 10^8$ |
| 93% apple/7% pomegranate | 18 | $3.3 \times 10^8$ |
| 90% apple/10% pomegranate | 18 | $5.3 \times 10^8$ |

TABLE 3b

*Lactobacillus paracasei* 8700:2, $1 \times 10^9$ Cfu/serving.

| Fruit juice components (wt %) | $CO_2$ (%) | L paracasei (CFU/250 ml) |
|---|---|---|
| 100% apple/ | 12 | $5.00 \times 10^9$ |
| 99% apple/1% pomegranate | 9 | $4.50 \times 10^7$ |
| 97% apple/3% pomegranate | 9 | $1.00 \times 10^7$ |
| 95% apple/5% pomegranate | 7 | $3.75 \times 10^6$ |
| 93% apple/7% pomegranate | 7 | $2.50 \times 10^6$ |
| 90% apple/10% pomegranate | 7 | $<2.50 \times 10^6$ |

TABLE 3c

*Lactobacillus rhamnosus* 271, $1 \times 10^9$ CFU/serving.

| Fruit juice components (wt %) | $CO_2$ (%) | L rhamnosus (CFU/250 ml) |
|---|---|---|
| 100% apple/ | 20 | $4.00 \times 10^9$ |
| 99% apple/1% pomegranate | 8 | $<2.50 \times 10^6$ |
| 97% apple/3% pomegranate | 7 | $<2.50 \times 10^6$ |
| 95% apple/5% pomegranate | 7 | $<2.50 \times 10^6$ |
| 93% apple/7% pomegranate | 7 | $<2.50 \times 10^6$ |
| 90% apple/10% pomegranate | 6 | $<2.50 \times 10^6$ |

Other probiotic fruit juice drinks that have been prepared are the following.

Orange/Acerola (100% Juice)

| Orange | 95% |
|---|---|
| Acerola | 5% |

*Lactobacillus paracasei* 8700:2/*Lactobacillus plantarum* HEAL 9 present in total amount of $1 \times 10^9$ CFU/serving Apple/Cranberries (100% Juice)

| Apple | 99.5% |
|---|---|
| Cranberries | 0.5% |

*Lactobacillus paracasei* 8700:2/*Lactobacillus plantarum* HEAL 9 present in total amount of $1 \times 10^9$ CFU/serving.

Impact of Acerola on the Metabolism on Different Probiotic Bacteria in Orange Juice and Apple Juice.

Different amounts of a gas formation reducer (acerola; 5, 10, 20 or 30 weight %) was added to a primary juice (orange juice). After mixing the gas formation reducer and primary juice the resulting juices were heat-treated according to the experimental set-up above. The fruit juice mixtures were then inoculated with probiotic bacteria (the mixture of *Lactobacillus plantarum* HEAL 9 and *Lactobacillus paracasei* 8700: 2; *Lactobacillus plantarum* HEAL 9; *Lactobacillus plantarum* 299v or *Lactobacillus rhamnosus* 271).

Other gas formation reducers are expected to act reducing on the carbon dioxide production. Therefore, the gas formation reducers aronia, blackcurrant, buckthorn, or elderberry will be tested in juice drinks experiments with any of the primary juices such as orange juice, lemon juice, grapefruit juice, lime juice, apple juice or pear juice in the presence of probiotics.

In a further experiment orange juice with aronia (5%) or sloe (5%) was produced and compared to a pure orange juice. *Lactobacillus plantarum* HEAL 9 and *Lactobacillus paracasei* 8700 was used as probioitics in all the juices. The amount added of each bacteria was $2 \times 10^6$ CFU/ml.

The CFU was measured weekly and a sensory evaluation was made after 1 week and 3 weeks, respectively.

|  | CFU/ml, 1 w | CFU/ml, 2 w | CFU/ml, 3 w | Sensory evaluation 1 w | Sensory evaluation 3 w |
|---|---|---|---|---|---|
| Orange juice | $7.4 \times 10^6$ | $3.1 \times 10^7$ | $7.7 \times 10^7$ | OK | Gas, diacethyl formation |
| Orange + 5% aronia | $6.7 \times 10^6$ | $3.7 \times 10^7$ | $8.2 \times 10^7$ | OK | OK, minor acidic |
| Orange + 5% sloe | $6.6 \times 10^6$ | $3.7 \times 10^7$ | $6.5 \times 10^7$ | OK | OK, minor acidic |

The orange juice with 5% aronia or 5% sloe was ok both after 1 week and after 3 weeks with no gas production in contrary to the pure orange juice which had a unpleasant diacethyl taste after 3 weeks and had also produced undesirable gas. The aronia and sloe, respectively, inhibits the metabolism but not the growth of the probiotics present as can be seen in the table above.

Large Scale Production of Probiotic Orange Juice

A probiotic orange juice with and without 5% acerola was produced in a large scale of 5000 liters. *Lactobacillus plantarum* HEAL 9 and *Lactobacillus paracasei* 8700 was used as probiotics.

The stability of the juice was followed during several weeks. After production the juice was packaged into 1 liter packages and stored at 8° C.

|  | CFU/ml start | CFU/ml, 1 week | CFU/ml, 2 weeks | CFU/ml, 3 weeks | CFU/ml, 4 weeks |
|---|---|---|---|---|---|
| Orange | $4.9 \times 10^6$ | $5.8 \times 10^6$ | $2.9 \times 10^7$ | $2.8 \times 10^7$ | $1.5 \times 10^7$ |
| Orange + 5% acerola | $2.9 \times 10^6$ | $2.2 \times 10^6$ | $5.3 \times 10^5$ | $7.9 \times 10^6$ | $4.6 \times 10^7$ |

|  | Sensory eval. 1 week | Sensory eval. 2 week | Sensory eval. 3 week | Sensory eval. 4 week |
|---|---|---|---|---|
| Orange juice |  | Gas, diacethyl | Gas, diacethyl | Gas, diacethyl |
| Orange + 5% acerola | OK | OK | OK | OK |

The large scale production functions as expected, i.e. that the pure probiotic orange juice produces the undesirable gas and diacethyl, whereas the orange juice with the 5% acerola remains ok with no problems regarding gas or diacethyl production.

The invention claimed is:

1. A probiotic fruit juice drink, consisting of:
   at least one species of probiotic bacteria of *Lactobacillus* is one selected from the group consisting of *Lactobacillus plantarum* 299 (DSM 6595), *Lactobacillus plantarum* 299v (DSM 9843), *Lactobacillus plantarum* HEAL 9 (DSM 15312), *Lactobacillus plantarum* HEAL 19 (DSM 15313), *Lactobacillus plantarum* HEAL 99 (DSM 15316), *Lactobacillus paracasei* 8700:2 (DSM 13434), *Lactobacillus paracasei* 02A (DSM 13432) and *Lactobacillus rhamnosus* 271 (DSM 6594);
   at least one gas formation reducer selected from the group consisting of acerola, pomegranate, cranberry, sloe, and any combinations thereof;
   a primary fruit juice chosen from citrus fruit juice or pip fruit juice;
   a secondary fruit juice; and
   water.

2. The probiotic fruit juice drink according to claim 1, wherein the citrus fruit juice is one selected from the group consisting of orange juice, lemon juice, grapefruit juice, and lime juice.

3. The probiotic fruit juice drink according to claim 1, wherein the pip fruit juice is chosen from apple juice or pear juice.

4. The probiotic fruit juice drink according to claim 1, wherein the at least one species of probiotic bacteria of *Lactobacillus* is present in the fruit juice drink in an amount of about $1 \times 10^5$ to about $1 \times 10^{12}$ CFU per 250 mL.

5. The probiotic fruit juice drink according to claim 1, wherein the secondary fruit juice is one juice selected from the group consisting of pineapple juice, mango juice, banana juice, white grape juice, peach juice, apricot juice, passion fruit juice, watermelon juice, raspberry juice, strawberry juice, blueberry juice, blackberry juice, kiwi juice, guava juice and any mixtures thereof.

6. The probiotic fruit juice drink according to claim 1, wherein the proportion of the primary fruit juice is present in the range of about 50-99.5% (w/w),
   the gas formation reducer is present in the range of about 0.5-40% (w/w),
   the added water is present in the range of about 1-10% (w/w), and
   the secondary fruit juice is present in the range of 0-10% (w/w).

7. The probiotic juice drink according to claim 1, wherein the juice drink further comprises added vitamin C.

8. A method of producing a probiotic fruit juice, comprising:
   mixing,
      at least one gas formation reducer selected from the group consisting of acerola, pomegranate, cranberry, sloe, and any combinations thereof,
      at least one species of probiotic bacteria of *Lactobacillus* is one selected from the group consisting of *Lactobacillus plantarum* 299 (DSM 6595), *Lactobacillus plantarum* 299v (DSM 9843), *Lactobacillus plantarum* HEAL 9 (DSM 15312), *Lactobacillus plantarum* HEAL 19 (DSM 15313), *Lactobacillus plantarum* HEAL 99 (DSM 15316), *Lactobacillus*

*paracasei* 8700:2 (DSM 13434), *Lactobacillus paracasei* 02A (DSM 13432) and *Lactobacillus rhamnosus* 271 (DSM 6594), a primary fruit juice chosen from citrus fruit juice or pip fruit juice, a secondary fruit juice, and water.

9. The method according to claim 8, wherein the citrus fruit juice is one selected from the group consisting of orange juice, lemon juice, grapefruit juice, and lime juice.

10. The method according to claim 8, wherein the pip fruit juice is chosen from apple juice or pear juice.

11. The method according to claim 8, wherein the at least one species of probiotic bacteria of *Lactobacillus* is present in the fruit juice drink in an amount of about $1 \times 10^5$ to about $1 \times 10^{12}$ CFU per 250 mL.

12. The method according to claim 8, wherein the secondary fruit juice is one juice selected from the group consisting of pineapple juice, mango juice, banana juice, white grape juice, peach juice, apricot juice, passion fruit juice, watermelon juice, raspberry juice, strawberry juice, blueberry juice, blackberry juice, kiwi juice, guava juice and any mixtures thereof.

13. The method according to claim 8, wherein the proportion of the primary fruit juice is present in the range of about 50-99.5% (w/w), the gas formation reducer is present in the range of about 0.5-40% (w/w), the added water is present in the range of about 1-10% (w/w), and the secondary fruit juice is present in the range of 0-10% (w/w).

14. The method according to claim 8, wherein the juice drink further comprises added vitamin C.

15. The probiotic fruit juice drink according to claim 4, wherein the at least one species of probiotic bacteria of *Lactobacillus* is present in the fruit juice drink in an amount of about $1 \times 10^6$ to about $1 \times 10^{10}$ CFU per 250 mL.

16. The probiotic fruit juice drink according to claim 4, wherein the at least one species of probiotic bacteria of *Lactobacillus* is present in the fruit juice drink in an amount of about $1 \times 10^7$ to about $1 \times 10^9$ CFU per 250 mL.

17. The method according to claim 11, wherein the at least one species of probiotic bacteria of *Lactobacillus* is present in the fruit juice drink in an amount of about $1 \times 10^6$ to about $1 \times 10^{10}$ CFU per 250 mL.

18. The method according to claim 11, wherein the at least one species of probiotic bacteria of *Lactobacillus* is present in the fruit juice drink in an amount of about $1 \times 10^7$ to about $1 \times 10^9$ CFU per 250 mL.

* * * * *